United States Patent [19]

Iino et al.

[11] Patent Number: 4,824,548
[45] Date of Patent: Apr. 25, 1989

[54] ELECTROCHEMICAL GAS SENSOR

[75] Inventors: Atsushi Iino, Nagoya; Nobuhide Kato, Aichi, both of Japan

[73] Assignee: NGK Insulators, Ltd., Nagoya, Japan

[21] Appl. No.: 26,433

[22] Filed: Mar. 16, 1987

[30] Foreign Application Priority Data

Mar. 17, 1986 [JP] Japan .................................. 61-58875

[51] Int. Cl.4 ............................................ G01N 27/58
[52] U.S. Cl. .................................... 204/406; 204/410; 204/412; 204/425
[58] Field of Search ............... 204/410, 412, 425, 426, 204/1 S, 406

[56] References Cited

U.S. PATENT DOCUMENTS 4,559,126 12/1985 Mase et al. .......................... 204/425

FOREIGN PATENT DOCUMENTS

| 0068321 | 1/1983 | European Pat. Off. | ............ 204/425 |
| 0134709 | 3/1985 | European Pat. Off. | ............ 204/425 |
| 0133820 | 3/1985 | European Pat. Off. | ............ 204/425 |
| 0162603 | 11/1985 | European Pat. Off. | ............ 204/425 |
| 0172746 | 2/1986 | European Pat. Off. | ............ 204/425 |
| 0171910 | 2/1986 | European Pat. Off. | ............ 204/425 |
| 58-153155 | 9/1983 | Japan | ............ 204/426 |
| 58-172542 | 10/1983 | Japan | ............ 204/426 |

Primary Examiner—G. L. Kaplan
Attorney, Agent, or Firm—Parkhurst, Oliff & Berridge

[57] ABSTRACT

An electrochemical device for detecting a measurement fluid, which includes a planar solid electrolyte body, a first electrode formed on the planar solid electrolyte body and substantially exposed to the measurement fluid, a second electrode formed on the planar solid electrolyte body and substantially isolated from the measurement fluid, a porous layer disposed in direct contact with the second electrode, and a device for applying an electric current so as to flow from the second electrode to the first electrode. The device may further include a third electrode, and a fourth electrode substantially directly exposed to the measurement fluid. In this case, the first and third electrodes are exposed to the measurement fluid through a thin flat space or porous layer having a predetermined diffusion resistance to the measurement fluid, and a current regulating device is connected between the third and fourth electrodes, for controlling an atmosphere adjacent to the first electrode.

26 Claims, 12 Drawing Sheets

ELECTROCHEMICAL GAS SENSOR

BACKGROUND OF THE INVENTION

1. Field of the Invention

The present invention relates in general to an electrochemical device, and more particularly to an oxygen sensor for detecting the concentration of oxygen in a measurement fluid, in particular, exhaust gases emitted by an internal combustion engine.

2. Discussion of the Prior Art

There has been known a sensing device including an electrochemical element having a solid electrolyte body, for example, an oxygen sensor which detects or determines the oxygen concentration of exhaust gases emitted from an internal combustion engine, for the purpose of controlling the combustion or fuel burning conditions of the engine according to signals produced by the oxygen sensor, and thereby purifying the exhaust gases and reducing the fuel consumption of the engine. An example of such oxygen sensors uses a sensing element which comprises a body of oxygen-ion conductive solid electrolyte such as zirconium oxide doped with calcium oxide or yttrium oxide, and which further comprises siutable electrodes formed on opposite surfaces of the solid electrolyte body. In this oxygen sensor, one of the electrodes is exposed to a reference gas such as the ambient air, while the other electrode is exposed to a desired measurement fluid such as exhaust gases. In operation, the oxygen sensor produces an output signal representative of an electromotive force induced between the two electrodes according to the principle of an oxygen concentration cell.

In recent years, there has been an increasing tendency to use an elongate planar sensing element, rather than a conventionally used tubular sensing element, in view of ease of fabrication and structural simplicity of the sensor. Such an elongate planar sensing element has, at its one longitudinal end, an oxygen detecting portion which is exposed to exhaust gases or other measurement fluids. Such planar oxygen sensing elements or oxygen sensors incorporating a planar oxygen sensing element are disclosed, for example, in Laid-Open Publications No. 58-153155 and 58-172542 (published in 1983) of Japanese Patent Applications.

In the electrochemical device exemplified by the oxygen sensors described above, one of the electrodes provided at the detecting portion of the sensing element functions as a measuring electrode to be exposed to the measurement fluid, while the other electrode functions as a reference electrode to be exposed to a reference gas which is present in a reference-gas space or passage formed in the sensing element so as to extend toward the detecting portion. The reference-gas space is open at the longitudinal end of the sensing element remote from the detecting portion, so that the reference-gas space communicates with the ambient air or atmosphere, through air-inlet openings formed through a housing in which the sensor is accommodated. In this arrangement, the ambient air is introduced as a reference gas into the reference-gas space within the sensing element, so that the reference electrode is exposed to the introduced reference gas.

However, the oxygen sensors constructed as described above tend to suffer from various inconveniences due to entry of undesirable external foreign substances such as water, salt water and muds, through the air-inlet openings provided in the sensor housing. These foreign substances may have adverse effects on the sensing element. For example, these substances may cause electrical insulation failure or similar trouble, which leads to inaccurate output signals of the sensor, or which results in damaging the sensing element due to rupture or breakage of the ceramic components.

Another drawback experienced in the oxygen sensors indicated above arises from the presence of the reference-gas space or passage which extends through the sensing element over its substantially entire length, which therefore reduces the structural strength of the sensing element.

In another type of oxygen sensor, the entirety of the sensing element is located within the measurement fluid, such that the measuring electrode is exposed to the measurement fluid, while the reference electrode communicates with the measurement fluid, either directly, or indirectly via a porous layer or diffusion-resistance layer having a given diffusion resistance to the measurement fluid. In this arrangement, the reference oxygen is continuously supplied to the reference electrode by a pumping cell of the sensing element, while at the same time the supplied reference oxygen is discharged into the external measurement fluid through the porous layer indicated above or other means. In this case, the reference gas to which the reference electrode is exposed is easily influenced by the ambient atmosphere, and the sensor output is accordingly influenced. If a large amount of pumping current is applied to the pumping cell to avoid such influences, the ceramic components of the sensing element are likely to be deteriorated, or the detecting accuracy of the sensor is lowered due to an excessive voltage drop caused by the adjustment of the reference gas. Further, the application of an excessive current to the pumping cell may cause separation or flake-off of the sensing element at the reference electrode.

SUMMARY OF THE INVENTION

It is accordingly an object of the present invention to provide an improved electrochemical device which is substantially free of the inconveniences described above.

According to the present invention, there is provided an electrochemical device for detecting a measurement fluid such as a gas, the electrochemical device comprising a planar solid electrolyte body, a first electrode disposed on the planar solid electrolyte body such that the first electrode is substantially exposed to the measurement fluid, a second electrode disposed on the planar solid electrolyte body such that the second electrode is substantially isolated from the measurement gas, a porous layer disposed in direct contact with the second electrode, and means for applying an electric current between the first and second electrode, so that the current flows from the second electrode to the first electrode.

According to another aspect of the invention, there is provided an electrochemical device for detecting a measurement fluid, the electrochemical device comprising at least one planar solid electrolyte body, diffusion-resistance means providing a predetermined diffusion resistance to the molecules of said measurement fluid, a first electrode disposed on the above at least one planar solid electrolyte body such that the first electrode is exposed to the measurement fluid through the diffusion-resistance means, a second electrode disposed on the above at least one planar solid electrolyte body such that the second electrode is substantially isolated from the measurement fluid, a third electrode disposed on the above at least one planar solid electrolyte body such that the third electrode is exposed to the measurement fluid through the diffusion-resistance means, a fourth electrode substantially directly exposed to the measurement fluid, a porous layer disposed in direct contact with the second electrode, means for applying an electric current between the first and second electrodes so that the current flows from the second electrode to the first electrode, and current regulating means connected between the third and fourth electrodes, for controlling an atmosphere adjacent to the first electrode.

According to a further aspect of the invention, there is provided an electrochemical device for detecting a measurement fluid, the electrochemical device comprising at least one planar solid electrolyte body, diffusion-resistance means having a predetermined diffusion resistance to the molecules of the measurement fluid, a first electrode formed on the above at least one planar solid electrolyte body and exposed to the measurement fluid through the diffusion-resistance means, a second electrode formed on the above at least one planar solid electrolyte body and substantially isolated from the measurement fluid, a third electrode formed on the above at least one planar solid electrolyte body and exposed to the measurement fluid through the diffusion-resistance means, a fourth and a fifth electrode which are substantially directly exposed to the measurement fluid, a porous layer disposed in direct contact with the second electrode, means for applying an electric current so as to flow from the second electrode to one of the first and fifth electrodes, voltage detecting means connected between the second and at least one of the first and fifth electrodes, for detecting a voltage therebetween, and current regulating means connected beween the third and fourth electrodes, for controlling an atmosphere adjacent to the first electrode.

According to one feature of the invention, the electrochemical device further comprises a heater which is embedded in an electrically insulating portion of the porous layer. The heater is adapted to heat a detecting portion of a sensing element of the device, and thereby hold the detecting portion at a suitable operating temperature even while the temperature of the measurement fluid is low. The detecting portion includes a portion of the solid electrolyte body or bodies on which the electrodes are disposed or formed. The heater assures an accurate and reliable operation of the sensing element.

According to another feature of the invention, the external measurement fluid diffuses into the sensing element under a predetermined diffusion resistance, so that the first and third electrodes are exposed to the diffused measurement fluid. The diffusion-resistance means may be provided by forming a thin flat space between the first and third electrodes, such that the thin flat space communicates with the external measurement fluid. Alternatively, the diffusion-resistance means may be constituted by a porous structure disposed between the first and third electrodes.

In accordance with a further feature of the invention, the means for applying an electric current between the electrodes includes a constant-voltage or constant-current power source. In the case where a heater is provided in the electrochemical device, a single power source may be used to energize both the heater, and the first and second electrodes. In this case, a voltage divider is provided for applying a fraction or portion of the total voltage of the power source between the first and second electrodes.

According to a still further feature of the invention, two other electrodes are spaced from the first and second electrodes, and are disposed on opposite surfaces of the planar solid electrolyte body on which the first and second electrodes are disposed, or on another planar solid electrolyte body. One of these other electrodes is positioned so as to be exposed to the measurement fluid, while the other one is exposed to a space in which the porous layer is accommodated and which is substantially isolated from the external measurement fluid. In one form of this arrangment, a heater is embedded in an electrically insulating portion of the porous layer. The heat generating element of the heater may be at least partially embedded in a highly dense gas-tight material incorporated in the porous layer.

In accordance with a yet further feature of the invention, the second electrode is formed in contact with the porous layer, or is spaced apart from the porous layer by a thin flat space or gap formed therebetween. In the latter case, a reservoir member may be disposed between the second electrode and the porous layer, so as to define therebetween a reservoir for storing a reference gas. The reservoir member may have an opening such as a slot which communicates with the porous layer and the reservoir.

According to another feature of the invention, at least one of the electrodes disposed on an outer surface of the planar solid electrolyte body or bodies and exposed to the measurement fluid is covered by a porous protective layer. This protective layer may be formed by plasma spraying. The protective layer may consist of a porous ceramic layer which is formed by co-firing an unfired ceramic layer formed by printing on an unfired layer of the corresponding electrode, together with an unfired green sheet of the planar solid electrolyte body on which the unfired layer of the corresponding electrode is formed. Alternatively, the porous ceramic layer may be formed by preparing an unfired ceramic sheet, placing the unfired ceramic sheet on an unfired layer of the corresponding electrode, and then co-firing the unfired ceramic sheet together with the unfired layer of the corresponding electrode, and an unfired green sheet of the planar solid electrolyte body on which the unfired layer of the electrode is formed.

In accordance with a still further feature of the invention, the electrochemical device further comprises means for restricting a diffusion of a reference gas from the porous layer into the measurement fluid, or into an external space outside the sensing element which comprises the solid electrolyte body or bodies, electrodes and porous layer. In one form of this arrangement, this restricting means is constituted by filler means which holds the sensing element within a sensor housing in an air-tight manner.

BRIEF DESCRIPTION OF THE DRAWINGS

The foregoing and optional objects, features and advantages of the present invention will be better understood by reading the following detailed description of some preferred embodiments of the invention, when considered in conjunction with the accompanying drawings, in which.

DETAILED DESCRIPTION OF THE PREFERRED EMBODIMENTS

To further clarify the principle of the present invention, the preferred embodiments of the invention will be described in detail, by reference to the accompanying drawings.

Figure 1:
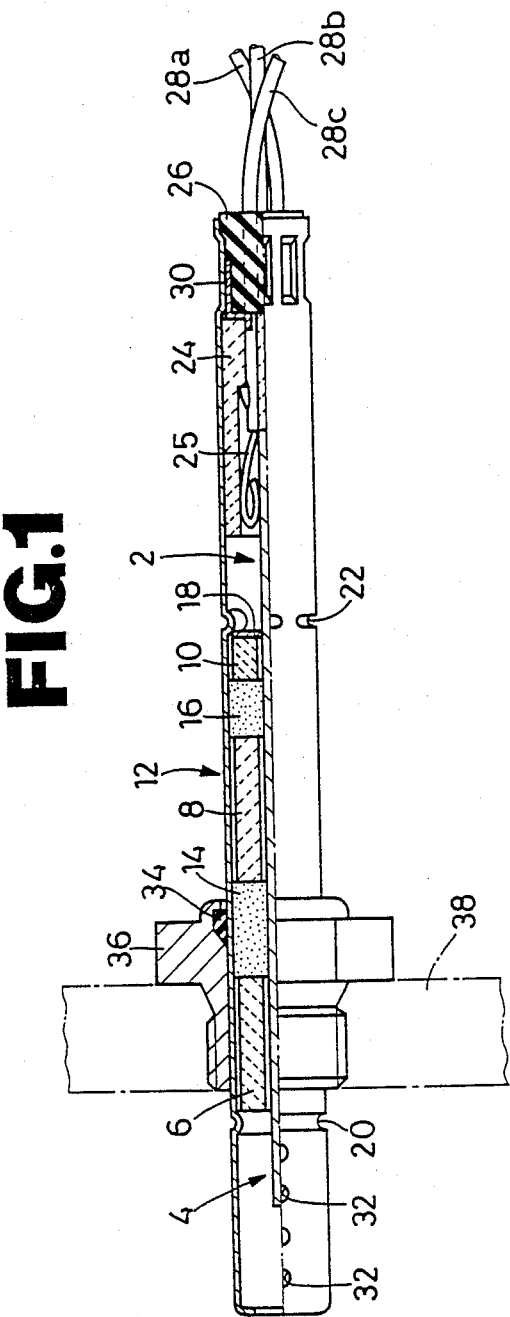
FIGS. 1 and 2 are schematic views partly in longitudinal cross section of different arrangements of an oxygen sensor of the present invention.

Referring first to FIG. 1, there is shown one arrangement of an oxygen sensor constructed according to the invention. In the figure, reference numeral 2 designates an oxygen sensing element whose primary component consists of an oxygen-ion conductive solid electrolyte such as stabilized zirconia. The oxygen sensing element 2 is a generally elongate planar member having a rectangular transverse cross sectional shape with a relatively small width. The sensing element 2 has an oxygen detecting portion 4 at a first longitudinal end (left-hand side end in FIG. 1). The oxygen detecting portion 4 produces an electrical signal according to the principle of an oxygen concentration cell. The electrical output is fed to an external device through electrical connections at a second longitudinal end (right-hand side end in FIG. 1) of the sensing element 2.

The elongate planar or plate-like oxygen element 2 having the oxygen detecting portion 4 adjacent to the first longitudinal end is supported at three spaced-apart positions along its longitudinally intermediate portion, by a first, a second and a third ceramic insulating member 6, 8, 10. These insulating members 6, 8 and 10 supporting the sensing element 2 are accommodated in one piece sensor housing in the form of a cylindrical protective tubing member 12 made of stainless steel or other metallic materials. The three ceramic insulating members 6, 8 and 10 are fixed in the protective tubing member 12, by two fillers such as talc in the form of a first air-tight filler 14 disposed between the first and second insulating members 6 and 8, and a second air-tight filler 16 disposed between the second and third insulating members 8 and 10. These two air-tight fillers 14, 16 have suitable lengths, and hold the sensing element 2 on the centerline of the protective tubing member 12.

In the arrangement described above, the sensing element 2 is held in the protective tubing member 12 such that the detecting portion 4 adjacent to the first longitudinal end is substantially air-tightly separated from the other or second longitudinal end by the air-tight fillers 14 and 16. The tubing member 12 is radially inwardly compressed at two longitudinally spaced-apart portions thereof, and is thus provided with a first and a second radially inward protrusion 20, 22, as shown in FIG. 1. These inward protrusions 20, 22 serve to prevent longitudinal displacements of the first insulating member 6, first air-tight filler 14, second insulating member 8, second air-tight filler 16, third insulating member 10 and a washer 18, within the protective tubing member 12.

A fourth ceramic insulating member 24 is positioned in the protective tubing member 12, such that the second longitudinal end portion of the sensing element 2 is inserted in the insulating member 24. This fourth insulating member 24 is fixed in position by a rubber plug 26 made of a fluoro-rubber which is press-fitted in the second longitudinal end of the protective tubing member 12. The second end portion of the tubing member 12 is not provided with air vents as provided in a conventional sensor, and is completely fluid-tightly sealed by the rubber plug 26 inserted in the opening. Three electrically conducting members in the form of lead wires 28a, 28b and 28c are passed through the rubber plug 26, extending into the fourth ceramic insulating member 24. Metallic connectors 25 are disposed in the fourth insulating member 24, for connecting the lead wires 28a, 28b, 28c to corresponding electrical leads which are connected to electrodes and an electrical heater of the sensing element 2. One of the electrodes of the element 2 is electrically connected to the tubing member 12 via an earth lead 30, and is thus grounded.

The protective tubing member 12 accommodating therein the sensing element 2 has a plurality of gas-inlet apertures 32 in the first end portion, so that gases to be measured are introduced through these apertures into the tubing member 12, and are directed to the oxygen detecting portion 4 of the sensing element 2.

The protective tubing member 12 is inserted through a bore formed in a retainer housing 36 which is threaded to a wall of a fluid conduit, for example, to a partition wall 38 of an exhaust pipe of an automotive vehicle. The tubing member 12 is air-tightly secured to the retainer housing 36 via an air-tight sealing ring 34 which is disposed between the outer surface of the tubing member 12 and the inner surface of the retainer housing 36. The protective tubing 12 and the retainer housing 36 are positioned relative to each other so that the air-tight sealing ring 34 is aligned with the first air-tight filler 14 in the longitudinal direction of the tubing member 12, and so that the first longitudinal end portion in which the oxygen detecting portion 4 of the sensing element 2 is accommodated is located within the fluid conduit, e.g., exhaust pipe. Thus, the tubing member 12 is attached to the partition wall 38 with fluid tightness maintained therebetween.

With the tubing member 12 attached to the partition wall 38, a measurement gas in the fluid conduit flows into the tubing member 12 through the gas-inlet apertures 32, so that a measuring electrode of the oxygen detecting portion 4 of the sensing element 2 in the tubing member 12 is exposed to the introduced measurement gas. At the same time, a reference electrode incorporated within the detecting portion 4 is exposed to a suitable reference gas. A difference in oxygen concentration between the measurement gas and the reference gas is detected as an electrical output which is represented by an electromotive force induced between the measuring and reference electrodes. The electrical output signal is obtained through the lead wire 28a and the earth lead 30. In the thus constructed oxygen sensor, the protective tubing member 12 serving as a housing for the sensing element 2 has no air vents communicating with the ambient air, as usually provided in a conventional oxygen sensor, as indicated above. In other words, the open end of the tubing member 12 remote from the detecting portion 4 is air-tightly sealed by the rubber plug 26, and is therefore protected against entry of water, salt water, muds and other external substances, which may cause insulation troubles leading to inaccurate output signals of the sensing element 2, and rupture of ceramic components and consequent breakage of the sensing element. The instant arrangement is effectively protected against such troubles.

Figure 2:
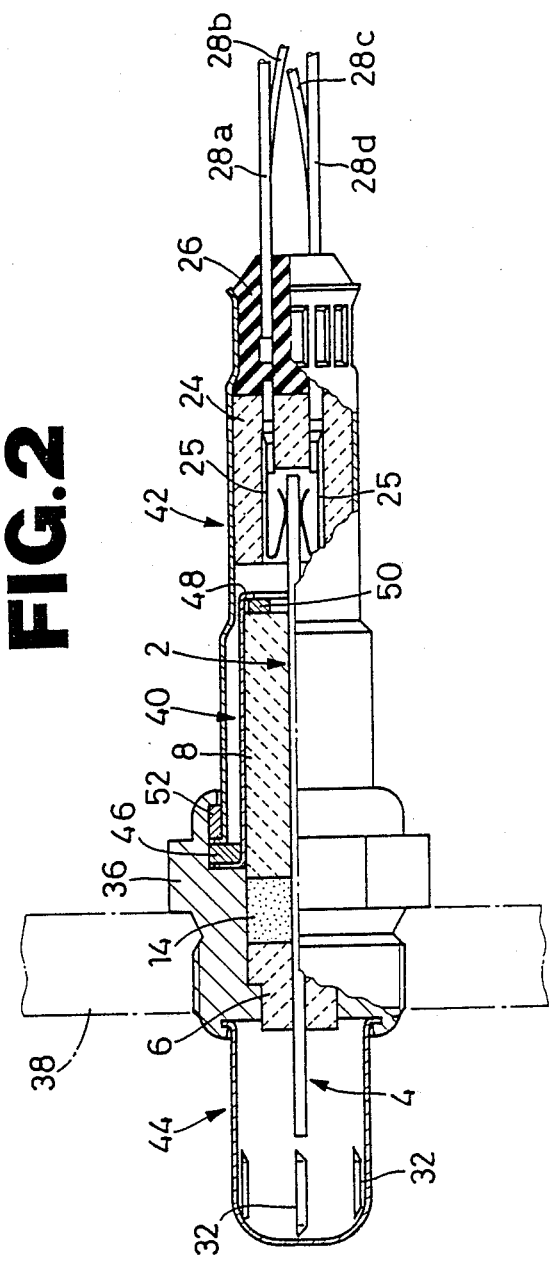

Referring next to FIG. 2, there is illustrated a modified construction of the oxygen sensor according to the present invention. In this modified construction, the portion of the oxygen sensing element 2 located outside the partition wall 38 is accommodated in an external sensor housing which consists of an inner tube 40 and an outer tube 42 which are made of a metallic material. The oxygen detecting portion 4 of the sensing element 2 exposed to the measurement gas is accommodated in an internal sensor housing in the form of a protective covering 44 which is separate from the external housing 40, 42. The protective covering 44 is secured to the retainer housing 38 by calking. The protective covering 44 has the gas-inlet apertures 32 which form a louver for introducing the measurement gas, so that the oxygen detecting portion 4 is exposed to the introduced gas.

The oxygen sensing element 2 shown in FIG. 2 is shorter than that of the preceding arrangement of FIG. 1. In this arrangement, the sensing element 2 is supported by the first and second ceramic insulating members 6 and 8, and one air-tight filler 14 of talc, for example, which fills the space between the first and second insulating members 6, 8. The inner tube 40 accommodating the second insulating member 8 is fixed at its one end to the retainer housing 36 by an inner-tube retaining ring 46, which is disposed between the inner surface of the retainer housing 36 and the outer surface of the inner tube 40. The other end 48 of the inner tube 40 is calked against the corresponding end of the second insulating member 8 via a sealing ring 50. Further, the outer tube 42 housing the inner tube 40 is fixed at its one end to the retainer housing 36 by calking of the housing 36 against the outer tube 42 via an outer-tube retaining ring 52, which is disposed between the calked end of the retainer housing 36 and the inner-tube retaining ring 46. The sensing element 2 projects a suitable distance from the calked end 48 of the inner tube 40, and their electrical leads are held in contact with the connectors 25 supported in the third insulating member 24 in the outer tube 42, whereby the sensing element 2 is electrically connected to the lead wires 28a, 28b, 28c, 28d. As in the preceding embodiment, the outer tube 42 has no air vents, and the open end of the outer tube 42 is air-tightly closed by the rubber plug 26. With the plug 26 radially inwardly compressed by the outer tube 42, the interior of the outer tube 42 is substantially air-tightly separated from the ambient air.

As in the preceding embodiment, the present oxygen sensor is also effectively protected against water and other external substances, and is substantially free from electrical insulation troubles, and breakage of the ceramic components, assuring improved reliability of the output signals.

Figure 3:
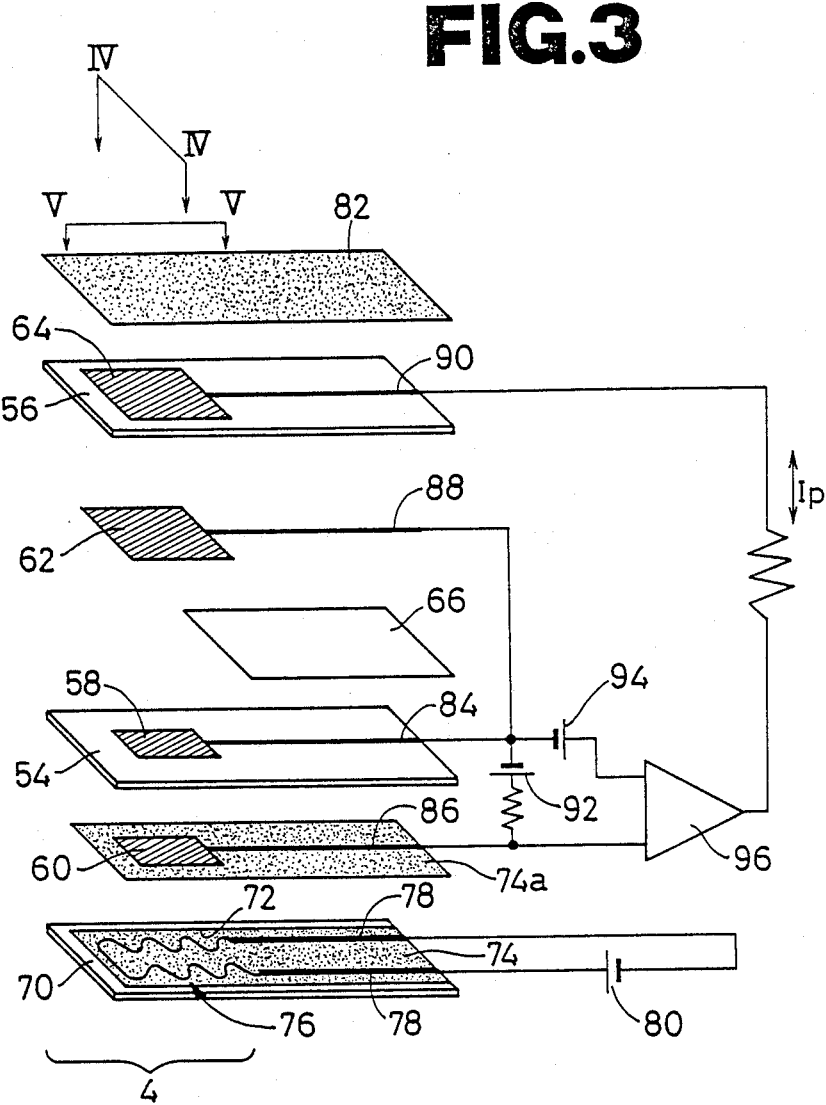
FIG. 3 is an exploded perspective view of one embodiment of an oxygen sensing element according to the invention.
Figure 4:
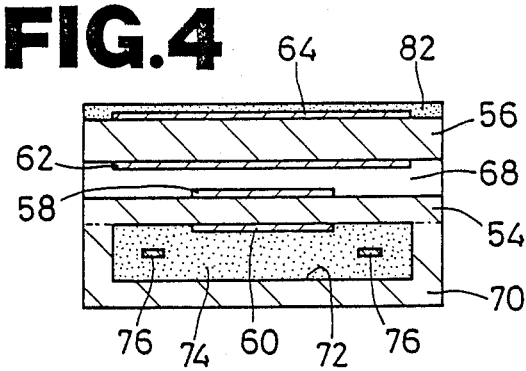
FIGS. 4 and 5 are elevational views in cross section taken along line IV—IV and line V—V of FIG. 3, respectively.
Figure 5:
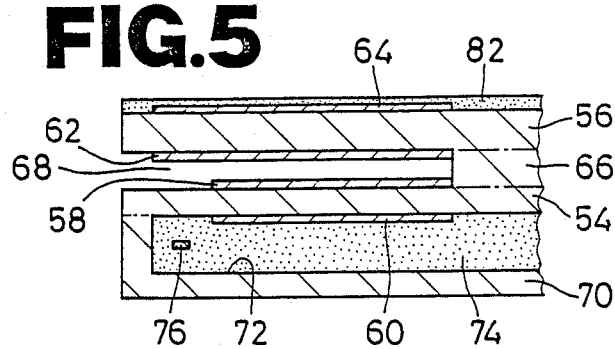

One example of the oxygen sensing element 2 usable in the completely fluid-tight housing structure as described above is illustrated in FIGS. 3-5, wherein reference numerals 54 and 56 designate planar solid electrolyte bodies made of zirconia containing yttria, or similar materials. On opposite major surfaces of the solid electrolyte body 54, there are formed a first and a second electrode 58, 60 in alignment with each other. Similarly, a third and a fourth electrode 62, 64 are formed on opposite major surfaces of the solid electrolyte body 56 in alignment with each other. These electrodes 58, 60, 62 and 64 are formed of platinum or other suitable metals. A ceramic spacer layer 66 made for example of zirconia is disposed between the two solid electrolyte bodies 54, 56, such that a thin flat space 68 is formed between the solid electrolyte bodies 54, 56, so that the first and third electrodes 58, 62 are exposed to an atmosphere in the thin flat space 68. This thin flat space 68 communicates with an external space in which the measurement gas exists, and the space 68 serves as diffusion-resistance means which has a predetermined diffusion resistance to the measurement gas. Thus, the measurement gas in the external space is diffused into the thin flat space 68 under the predetermined diffusion resistance, and the electrodes 58, 62 are exposed to the introduced measurement gas.

On one side of the solid electrolyte body 54 on which the second electrode 60 is formed, there is formed a gas-tight ceramic layer 70 made of zirconia or similar material, so that the second electrode 60 is protected or isolated from the external measurement gas. The ceramic layer 70 superposed on the solid electrolyte body 54 has a recess 72 which is filled with a porous, electrically insulating layer 74 made of alumina or other electrically insulating material, so that the solid electrolyte body 54 and the ceramic layer 74a are bonded together by the porous insulating layer 74. In this porous insulating layer 74, there is embedded a heater element 76 (heat generating element) for maintaining the first longitudinal end portion of the sensing element 2, i.e., oxygen detecting portion 4 at an optimum operating temperature. The heater element 76 is powered by an external power source 80 through leads 78, 78.

On one side of the solid electrolyte body 56 on which the fourth electrode 64 is formed, there is superposed a porous ceramic layer 82 through which the fourth electrode 64 is exposed to the measurement gas.

The electrodes 58, 60, 62 and 64 are electrically connected through respective leads 84, 86, 88 and 90 to external devices or functional means. Described more specifically, the first and second electrodes 58, 60 are connected through the leads 84, 86 to a DC power source 92, which functions as means for applying an electric current across the electrodes 58, 60 such that the current flows from the second electrode 60 to the first electrode 58. This DC power source 92 either has a constant voltage or provides a constant current.

The first electrode 58 and the third electrode 62 are connected via a reference power source 94, to an input of a differential amplifier 96 which functions as voltage detecting means and current regulating means. Further, the second electrode 60 is connected to another input of the differential amplifier 96, while an output of the amplifier 96 is connected to the fourth electrode 64. According to this arrangement, a pumping current (Ip) is applied between the third and fourth electrodes 62, 64 via the differential amplifier 96, based on an electromotive force induced between the first and second electrodes 58 and 60, as well known in the art, whereby the atmosphere adjacent to the third electrode 62 exposed to the thin flat space 68, in other words, the atmosphere adjacent to the first electrode 58 is controlled to be a desired atmosphere, for example, a stoichiometric atmosphere.

In the oxygen sensor arranged as described above, the DC power source 92 connected between the first and second electrodes 58, 60 produces a current flow in the direction from the second electrode 60 toward the first electrode 58. As a result, free oxygen and oxygen of compounds contained in the measurement gas within the thin flat space 68 are transferred, as oxygen ions, through the solid electrolyte body 54, from the first electrode 58 to the second electrode 60. The transferred oxygen is stored in the porous structure of the porous insulating layer 74 with which the second electrode 60 contacts. Namely, the stored oxygen serves as a reference gas to which the second electrod 60 is exposed. Therefore, the instant oxygen sensor does not require a conventionally required passage which communicates with the ambient air, for introducing the air as a reference gas to which the second electrode 60 is exposed. Thus, the second electrode 60 functions as a reference electrode exposed to the reference oxygen stored in the porous insulating layer 74 as a result of an oxygen pumping action by the electrodes 62, 64. On the other hand, the first electrode 58 exposed to the measurement gas within the thin flat space 68 functions as a measuring electrode. Based on a difference in oxygen concentration between the measurement gas and the reference gas to which the electrodes 58, 60 are exposed, a corresponding electromotive force is induced, and is detected by the differential amplifier 96 which functions as voltage detecting means. Based on the detected electromotive force, a corresponding pumping current Ip is applied between the third and fourth electrodes 58, 60 which serve as an electrochemical pumping cell, as well known in the art. In this manner, the atmosphere within the thin flat space 68, that is, the atmosphere adjacent to the first electrode 58 is controlled, and the measurement gas in the external space can be detected.

As explained above, the instant oxygen sensor eliminates the need of introducing the ambient atmosphere as a reference gas to the second or reference electrode 60. For this reason, the sensing element 2 can be completely fluid-tightly sealed or enclosed as shown in FIGS. 1 and 2. In the sensing element 2, a conventionally needed air passage is not present, and the recess 72 corresponding to such an air passage is filled with the porous insulating layer 74. Accordingly, the sensing element 2 has an improved strength, and can be easily manufactured because of the absence of a passage for introducing the ambient air.

In the thus constructed oxygen sensor, the oxygen in the thin flat space 68 is pumped out by a pumping action by the third and fourth electrodes 62, 64, while the oxygen in the external space is introduced into the thin flat space 68 through its thin opening, so that the third electrode 62 is exposed to the introduced oxygen. The rate of diffusion of the oxygen into the thin flat space 68 is restrained by the diffusion resistance of the thin flat space 68, whereby the oxygen partial pressure of the atmosphere within the thin flat space 68 can be made lower than that of the measurement gas in the external space. Therefore, the instant oxygen sensor can be advantageously used for detecting a measurement gas whose oxygen partial pressure is relatively high, for example, "lean-burned" exhaust gases emitted by an engine as a result of combustion of an air-fuel mixture whose air/fuel ratio is higher than the stoichiometric ratio.

However, the instant oxygen sensor may be used to detect the oxygen concentration of neutral exhaust gases which are produced as a result of combustion of an air-fuel mixture having the stoichiometric air-fuel ratio. Further, the sensor may be used to detect "rich-burned" exhaust gases which are produced in combustion of a fuel-rich air-fuel mixture whose air-fuel ratio is higher than the stoichiometric level, and which contain a large amount of unburned components or incombustibles. In this instance, the oxygen sensor is used as a so-called "rich-burn" sensor for sensing the combustion conditions of the engine, by sensing the unburned components contained in the exhaust gases. In either of the above cases, the neutral or rich-burned exhaust gases contain substantially no free oxygen, but contain oxygen of compounds produced in combustion of the air-fuel mixture, such as carbon monoxide and carbon dioxide, and oxygen of other compounds such as water vapor. The oxygen of such oxygen compounds is moved to the second electrode 60 by a pumping action effected between the first and second electrodes 58, 60, whereby a sufficient amount of oxygen is stored in the portion of the porous insulating layer 74 adjacent to the second electrode 60.

Where the measurement gas is a rich-burned exhaust gas, the incombustibles are introduced into the thin flat space 68, and the oxygen of the oxygen compounds is moved toward the third electrode 62 by a pumping action effected between the third and fourth electrodes 62, 64. As a result, the incombustibles in the thin flat space 68 are oxidized by the oxygen present adjacent to the third electrode 62, whereby the atmosphere within the space 68, that is, the atmosphere adjacent to the first electrode 58 is controlled to have substantially the same oxygen partial pressure as in the case where a lean-burned exhaust gas is introduced into the thin flat space 68.

Figure 6:
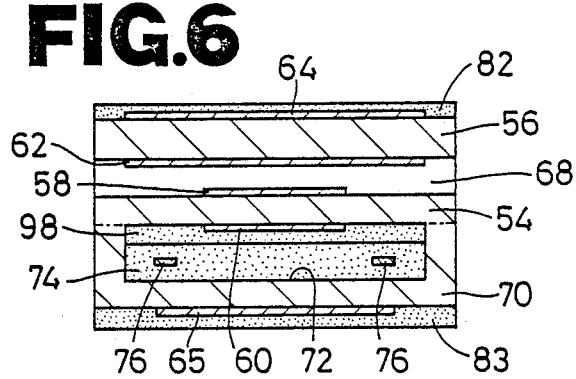
FIG. 6 is an elevational view corresponding to that of FIG. 4, showing another embodiment of the oxygen sensing element.

Referring further to FIG. 6, there is shown another example of the oxygen sensing element 2. This embodiment is different from the sensing element 2 of FIGS. 3–5 in that the recess 72 in the ceramic layer 70 is filled with two porous insulating layers 74, 98, and in that a fifth electrode 65 is formed on the outer surface of the gas-tight ceramic (solid electrolyte) layer 70. The fifth electrode 65 is covered by a porous protective layer 83. The porous insulating layer 98, which is made of zirconia, is formed between the solid electrolyte body 54 and the porous insulating layer 74, such that the second electrode 60 is embedded in the layer 98. More specifically, the porous zirconia insulating layer 98 prevents direct contact between the solid electrolyte body 54, and the porous insulating layer 74 made of alumina or similar ceramic material, and between the second electrode 60 and the porous insulating layer 74, thus avoiding separation or peel-off of the solid electrolyte body 54 and the porous insulating layer 74. Thus, an improved bonding strength is obtained between the solid electrolyte body 54, and the porous insulating layers 74, 98. In addition, the presence of the zirconia insulating layer 98 contributes to a reduced impedance between the second electrode 60 and the porous insulating layer 74. According to the present arrangement, the oxygen concentration of the measurement gas can be directly detected between the fifth electrode 65 and the second electrode 60. Further, the oxygen ions adjacent to the fifth electrode 65 may be moved as a reference gas toward the second electrode. The heater element 76 is embedded in the porous insulating layer 74 made of alumina or similar ceramic material.

Figure 7:
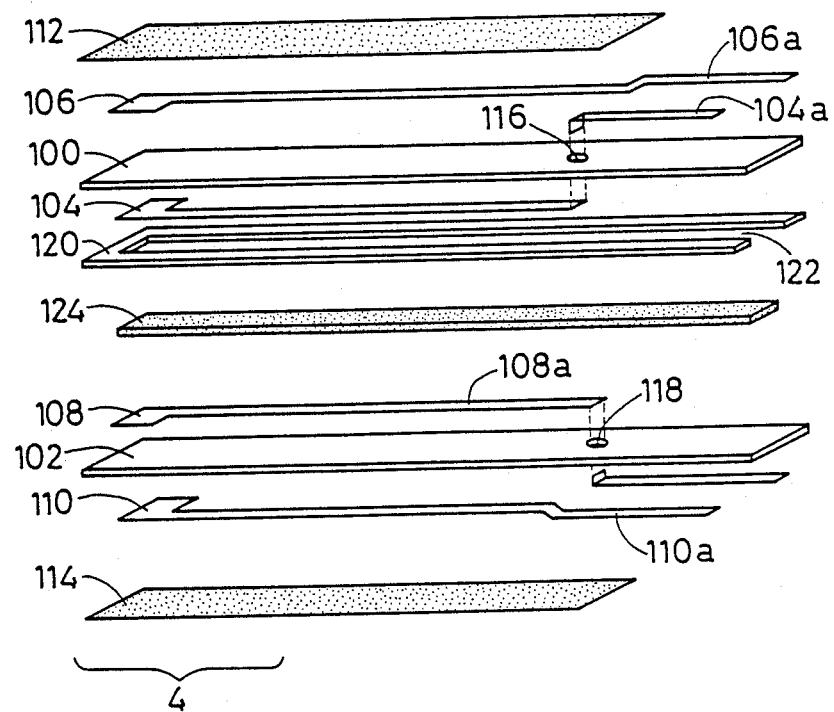
FIGS. 7 and 8 are exploded views in perspective of other embodiments of the oxygen sensing element according to the invention.

A further modified form of the oxygen sensing element according to the invention is depicted in FIG. 7, wherein one solid electrolyte body has measuring and reference electrodes formed thereon for measuring an electromotive force while another solid electrolyte body has two pumping electrodes formed thereon for supplying a reference gas (oxygen) to a porous layer contacting the reference electrode.

Described in greater detail, the sensing element 2 of FIG. 7 includes: a first and a second planar solid electrolyte body 100, 102; a reference electrode 104 and a measuring electrode 106 formed on opposite surfaces of the first solid electrolyte body 100; an inner electrode 108 and an outer electrode 110 formed on opposite surfaces of the second solid electrolyte body 102; a porous protective layer 112 covering the measuring electrode 106 exposed to the measurement gas; and another porous protective layer 114 covering the outer pumping electrode 110 also exposed to the measurement gas. The measuring and outer pumping electrodes 106, 110 are exposed to the measurement gas through the respective porous protective layers 112, 114. A lead 104a of the reference electrode 104 is passed through a hole 116 formed in the first solid electrolyte body 100, so that the terminal portion of the lead 104a is positioned on the same side of the body 100 as a lead 106a of the measuring electrode 106. Similarly, a lead 108a of the inner pumping electrode 108 is passed through a hole 118 formed in the second solid electrolyte body 102, so that the terminal portion of the lead 108a is positioned on the same side of the body 102 as a lead 110a of the outer pumping electrode 110. The leads 104a, 106a, 108a and 110a are connected to suitable external devices or means.

Between the first and second solid electrolyte bodies 100, 102, there is formed a gas-tight spacer member 120 which has an elongate rectangular slot 122. This slot 122 is open at its one longitudinal end remote from the electrodes 104, 108, and is closed at the other end such that the electrodes 104, 108 are aligned with the closed end portion of the slot 122. The slot 122 is filled with a porous layer 124, so that the reference electrode 104 and the inner pumping electrode 108 are held in contact with the opposite surfaces of the corresponding end portion of the porous layer 124.

In the oxygen sensing element constructed as described above, an electric current from an external power source is applied between the inner and outer pumping electrodes 108, 110, so as to flow in the direction from the inner pumping electrode 108 toward the outer pumping electrode, whereby the oxygen in the measurement gas is moved through the second solid electrolyte body 102, from the outer pumping electrode 110 exposed to the measurement gas, toward the inner pumping electrode 108 which contacts one of the opposite surfaces of the porous layer 124. Thus, the oxygen is stored in the porous layer 124, and the reference electrode 104 on the other surface of the porous layer 124 is exposed to the oxygen stored in the porous layer 124. As a result, an electromotive force is induced between the reference electrode 104, and the measuring electrode 106 exposed to the measurement gas, based on a difference in the oxygen concentration between the measurement gas and the reference gas in the porous layer 124. The induced electromotive force is fed to an external device via the leads 104a, 106a.

Figure 8:
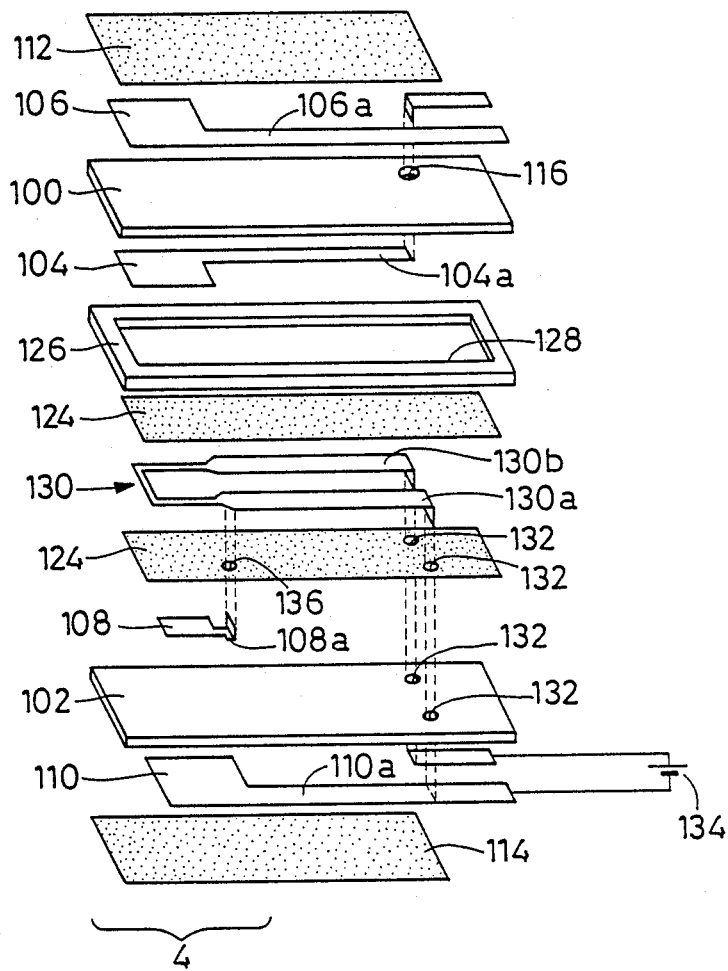

A still further modified form of the oxygen sensing element according to the invention is illustrated in FIG. 8, wherein the gas-tight spacer member 126 between the first and second solid electrolyte bodies 100, 102 takes the form of a rectangular frame having a rectangular opening 128. This rectangular opening 128 is filled with a pair of porous insulating layers 124, 124, and a heater element 130 sandwiched between the insulating layers 124. The reference electrode 104 and the inner pumping electrode 108 are held in contact with the respective porous insulating layers 124. Two holes 132 are formed through corresponding portions of the lower insulating layer 124 (in FIG. 8) and the second solid electrolyte body 102. Leads 130a, 130b of the heater element 130 are led to the outer surface of the solid electrolyte body 102, while being passed through the holes 132, and are connected to an external power source 134. The lead 108a of the inner pumping electrode 108 is passed through a hole 136 formed through the lower insulating layer 124, and is connected to the end of the lead 130a of the heater element 130. The lead 110a of the outer pumping electrode 110 is connected, on the outer surface of the second solid electrolyte body 102, to the terminal portion of the lead 130a to which the inner pumping electrode 108 is connected. Thus, a fraction of the total voltage of the power source 134 for the heater element 130 is applied between the inner and outer pumping electrodes 108, 110.

In the above arrangement, an electric current flows from the inner pumping electrode 108 to the outer pumping electrode 110, due to a divided portion of the voltage of the heater power source 134. Accordingly, the oxygen in the measurement gas is moved through the second solid electrolyte body 102 from the outer pumping electrode 110 exposed to the measurement gas, toward the inner pumping electrode 108, and the moved oxygen is stored in the porous insulating layers 124, as in the preceding sensing element of FIG. 7. Thus, the reference electrode 104 is exposed to the oxygen (reference gas) stored in the porous insulating layers 124.

Since the power source 134 for energizing the heater element 130 is tapped for applying a pumping voltage between the inner and outer pumping electrodes 108, 110, it is not necessary to increase the number of leads of the sensing element to be connected to the external devices. Accordingly, the number of the electrical connectors 25 (connected to the external lead wires 28) in the oxygen sensors of FIGS. 1 and 2 can be reduced. In the present arrangement of FIG. 8, the voltage of the power source 134 is divided by utilizing the electrical resistance of the heater element 130, in particular, their leads 103a, 130b. However, other methods are available to divide the source voltage. For example, a resistor circuit may be connected, as a voltage divider, to the power source 134, so that a desired fraction of the total voltage of the power source 134 may be obtained from the circuit. In this case, the maximum rate of movement of the oxygen from the outer pumping electrode 110 toward the inner pumping electrode 108 may be changed by selecting a suitable resistor incorporated in the circuit. This arrangement is effective to avoid an excessive amount of the oxygen stored in the porous insulating layers 124. Namely, the pumping current is reduced as the resistance of the resistor circuit is increased.

Figure 9:
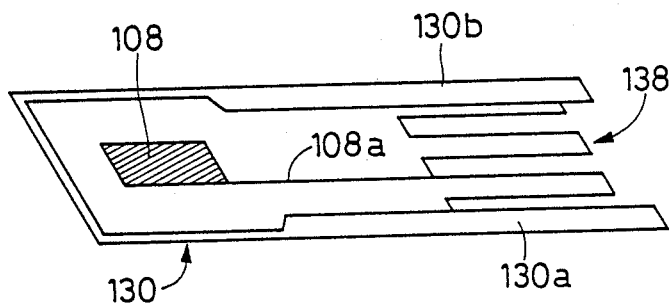
FIG. 9 is an illustration showing a manner of dividing a voltage of a heater power source.

A modified voltage divider is illustrated in FIG. 9, wherein a resistor pattern 138 having a suitable length is formed so as to connect the leads 130a and 130b of the heater element 130. The lead 108a of the inner pumping electrode 108 is connected to the resistor pattern 138, at a desired point along the length of the pattern. By changing the point of connection of the lead 108a to the resistor pattern 138, the electric current to be applied to the pumping electrodes 108, 110 can be easily adjusted. Further, the upper and lower limits of the oxygen amount to be pumped into the porous layers 124 can be set by adjusting the resistance of the resistor pattern 138, whereby an excessive feed of the oxygen and deterioration of the ceramic components of the sensor can be avoided. The resistor pattern connected across the leads 130a, 130b is not limited to that illustrated at 138 in FIG. 9, but various other patterns such as a thick-film resistor layer may be used.

In the oxygen sensor element of FIG. 8, the porous layers 124 for storing the oxygen pumped by the pumping electrodes 108, 110 is air-tightly enclosed by the rectangular frame-like spacer member 126 and the upper and lower solid electrolyte bodies 100, 102. However, an excessive rise in the pressure in the porous layers 124 due to continuous pumping of the oxygen by the pumping electrodes 108, 110 may be avoided, since the pressure may be released through the holes 116, 132 formed through the solid electrolyte bodies 100, 102. The pressure in the porous layers 124 may also be released by forming suitable pin holes through the spacer member 126. These pressure release holes or pin holes communicate with a suitable portion of the space within the sensor housing (one-piece tubing member 12, outer tube 42). Alternatively, the pressure release holes or pin holes may communicate with the measurement gas space inside the partition wall 38. In the latter case, however, care should be taken so that the pressure release holes or pin holes allow only an extremely small amount of diffusion flow of the measurement gas into the sensing element through the pressure release holes or pin holes.

In the oxygen sensors of FIG. 3 through 7, the pressure in the porous layers 74, 98, 124 is released through the end faces of the porous layers which is exposed to the space within the sensor housing (12, 42). The released pressure leaks, by natural diffusion, into the measurement gas space through minute pin holes in the fillers 14, 16, or into the atmosphere through minute gaps between the sensor housing and the inner components, or through the interiors of the lead wires 28. Of course, the pin holes in the fillers 14, 16, and the gaps leading to the atmosphere must be small enough to avoid entry of water and other foreign substances into the sensing element. Further, it is desirable that the pin holes and the gaps have a high diffusion resistance sufficient to restrict a diffusion of the reference gas (oxygen) from the porous layers 74, 98, 124 into the atmosphere or the measurement gas space. In particular, where the sensor is adapted such that the excessive oxygen leaks into the measurement gas space through the pin holes in the fillers 14, 16, the diffusion resistance of the pin holes must be high enough to substantially inhibit the release of the oxygen into the measurement gas space while the oxygen pressure in the porous layer 74, 98, 124 is relatively low. In the oxygen sensor according to the invention, the reference gas (oxygen) is stored in a comparatively large volume of space, because the porous layers 74, 98, 124 have large dimensions, and because a portion of the space within the sensor housing may be additionally used for storing the reference gas, as needed. Hence, the pressure release may be achieved by natural diffusion without providing special means for positively releasing the excessive pressure of the stored reference gas. However, the pumping cell for pumping the reference gas into the porous layers may be turned off as needed, so as to regulate the pressure of the reference gas stored within the sensing element.

Figure 10:
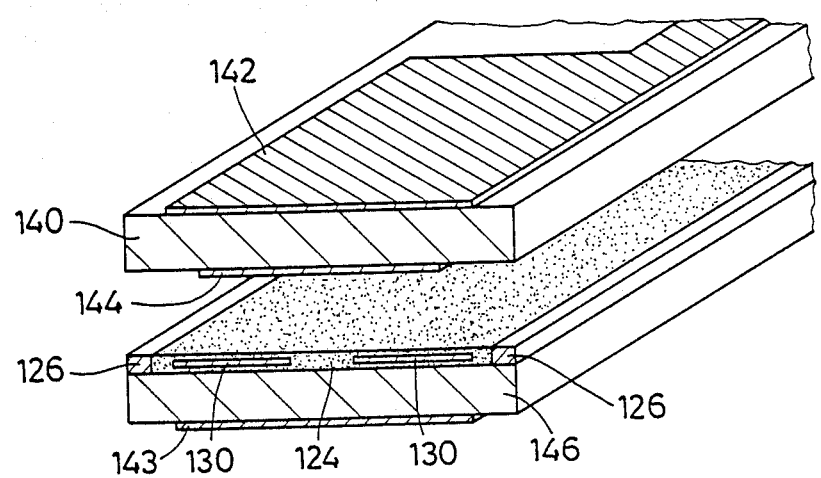
FIGS. 10 through 14 are fragmentary, exploded perspective views partly in cross section, of different embodiments of the oxygen sensing element according to the invention.

Different constructions off the oxygen detecting portion 4 of the sensing element 2 according to the present invention are illustrated in cross section in FIGS. 10 through 14, with the upper and lower parts separated from each other to show the intermediate porous layer 124. Referring first to FIG. 10, the sensing element includes a first and a second solid electrolyte body 140, 146 which have outer electrodes 142, 143 on their outer surfaces. These electrodes 142, 143 serve as measuring and pumping electrodes. The first solid electrolyte body 140 further has an inner electrode 144 on its inner surface. This inner electrode 144 functions as a reference and pumping electrode. As in the preceding arrangements, an electric current is applied between this inner electrode 144 and the outer electrode 142, and/or between the inner electrode 144 and the outer electrode 143. The porous layer 124 in which the heater element 130 is embedded is formed between the first and second solid electrolyte bodies 140, 146, such that the porous layer 124 is in contact with the inner electrode 144. The porous layer 124 is enclosed at its periphery by the gas-tight spacer member 126, and is sandwiched between the zirconia solid electrolyte bodies 140, 146. The spacer member 126 is made of an electrically conductive ceramic material such as zirconia.

In the oxygen sensing element of FIG. 10, oxygen in the external measurement gas is pumped toward the inner electrode 144, with an electric current flowing between the inner electrode 144 and at least one of the outer electrodes 142, 143. Thus, the oxygen is stored in the porous layer 124, as the reference gas to which the inner electrode 144 is exposed. An electromotive force is detected between the inner electrode 144 and at least one of the outer electrodes 142, 143. Since the outer electrodes 142, 143 serve as the measuring and outer pumping electrodes, the outer pumping electrodes may be covered by protective layers having a considerably high density, without affecting the operating response of the sensing element. Therefore, the electrode durability or life expectancy can be improved.

Figure 11:
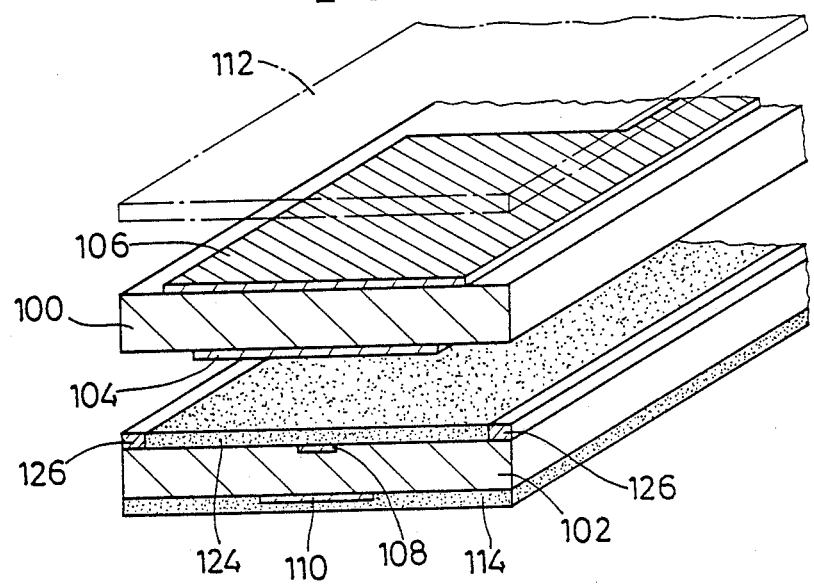

The oxygen sensing element shown in FIG. 11, which is similar in construction to the sensing element of FIG. 7, includes the measuring electrode 106, solid electrolyte body 100, reference electrode 104, porous layer 124, inner pumping electrode 108, solid electrolyte body 102, outer pumping electrode 110 and porous protective layer 114, these members being superposed on each other as shown in the figure. The porous layer 124 is isolated or insulated from the external measurement gas by the gas-tight spacer member 126. The protective layer 112 may be provided on the measuring electrode 106, if necessary. In this arrangement, too, the oxygen as a reference gas is stored in the porous layer 124, with an electric current applied between the two pumping electrodes 108, 110, while an electromotive force induced due to the oxygen concentration is detected between the measuring and reference electrodes 106, 104.

Figure 12:
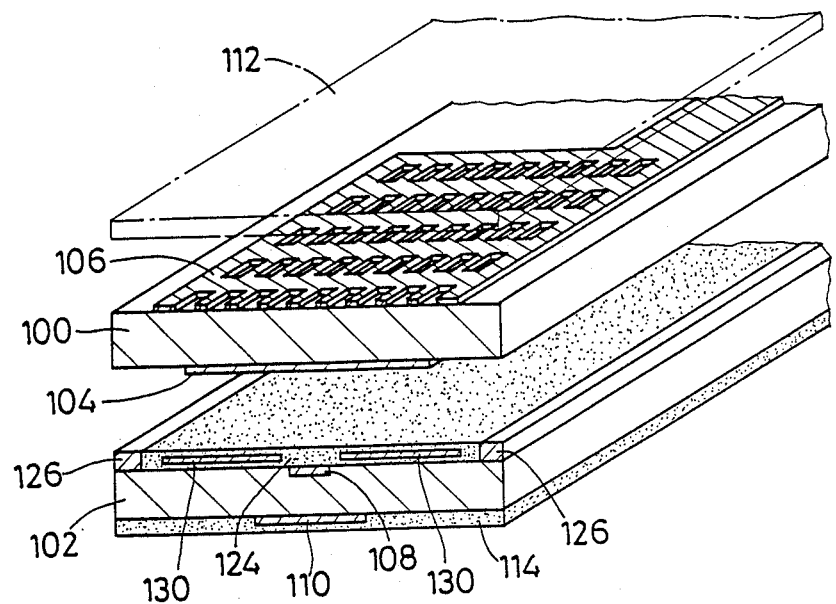

The sensing element of FIG. 12 is identical with that of FIG. 11, with the exception that the heater element 130 is embedded in the porous layer 124, for assuring an accurate and reliable operation of the oxygen detecting portion even when the temperature of the measurement gas is relatively low. For effective electrical insulation of the heater element 130 from the inner pumping electrode 108, these members 130, 108 are disposed such that they do not overlie each other as viewed in a plane parallel to the plane of the porous layer 124.

Figure 13:
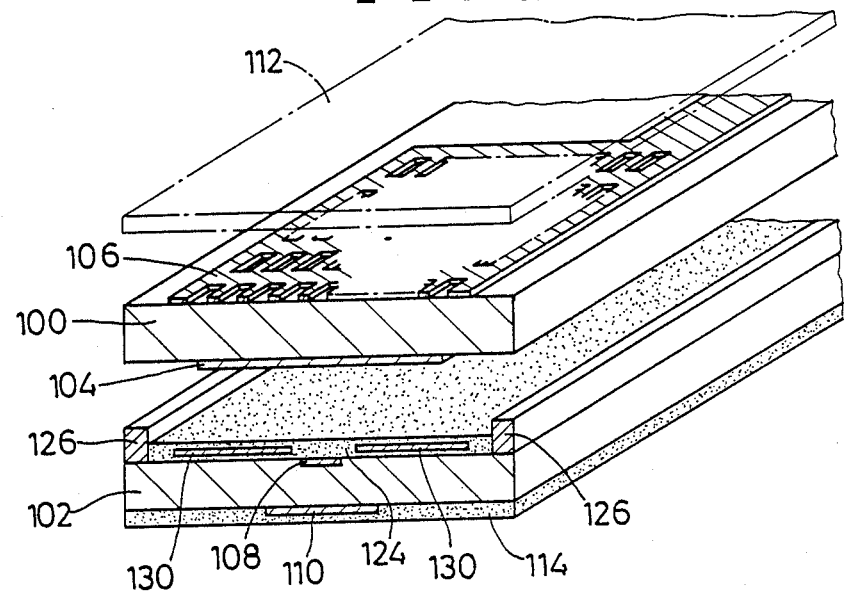

The sensing element of FIG. 13 is different from that of FIG. 12, in that the spacer 126 has a comparatively large thickness, in other words, the porous layer 124 has a comparatively small thickness, so that a thin flat space or gap is present between the porous layer 124 and the reference electrode 104. This gap assures improved electrical insulation between the reference electrode 104 and the heater element 130.

Figure 14:
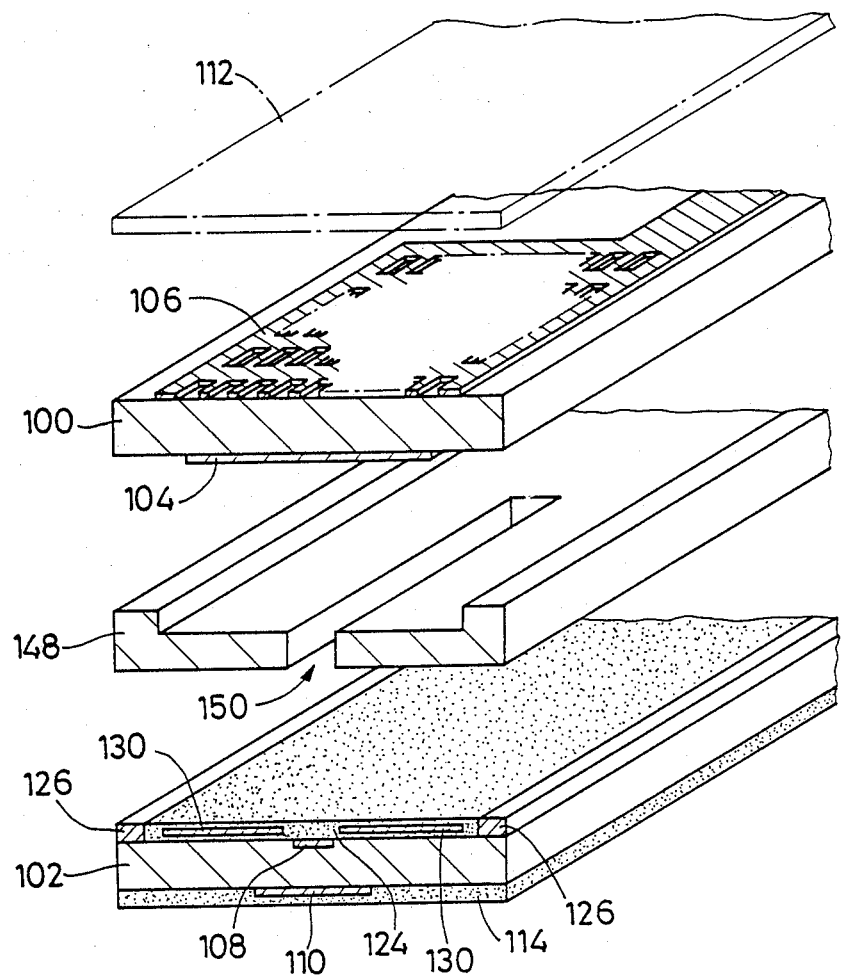

In the sensing element shown in FIG. 14, a gas-tight reservoir member 148 is interposed between the solid electrolyte 100, and the assembly of the porous layer 124 and the spacer member 126. The reservoir member 148, is made of zirconia or other ceramic material, cooperates with the reference electrode 104, to define a thin flat space or gap isolated from the external measurement gas. The reservoir member 148 has an opening in the form of a slot 150 through which the thin flat space communicates with the porous structure of the porous layer 124, whereby the thin flat space functions as a reservoir for storing the reference gas to which the reference electrode 104 is exposed.

In the oxygen sensing elements of FIG. 13 and 14, oxygen is moved through the porous layer 124 (and through the slot 150, in the arrangement of FIG. 14) and is stored in the thin flat space formed between the porous layer 124 and the reference electrode 104 (in the arrangement of FIG. 13) or between the reservoir member 148 and the reference electrode 104 (in the arrangement of FIG. 14), while the oxygen is moved toward the reference electrode 104 by a pumping action with an electric current flowing from the inner pumping electrode 108 toward the outer pumping electrode 110. Thus, the reference electrode 104 is exposed to the oxygen or reference gas stored in the thin flat space.

While the thin flat space formed between the reference electrode 104 and the porous layer 124 assures improved electrical insulation between the heater element 130 and the reference electrode 104, suitable provisions should be made for preventing the thin flat space from deteriorating a heat transfer from the heater element 130 toward the solid electrolyte body 100. For example, it is recommended that the frame-like spacer member 126, and/or the peripheral portion of the reservoir member 148, have a sufficiently large width so that the spacer and reservoir members 126, 148 may serve as thermal conductors. Alternatively, it is recommended that the thin flat space has a relatively small thickness of about 10-50 microns.

Figure 15:
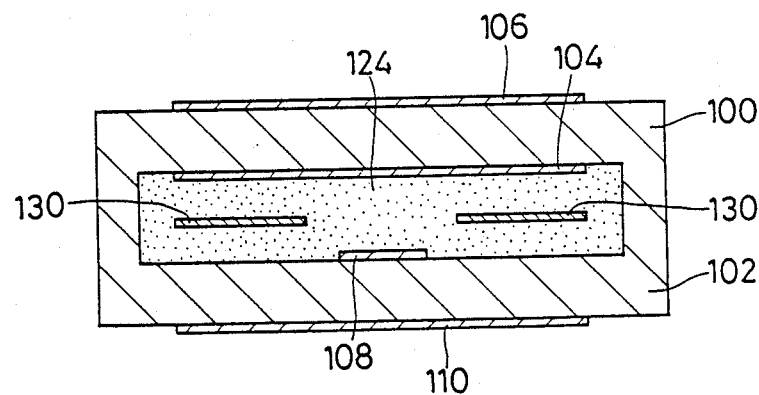
FIGS. 15 and 16 are elevational views in transverse cross section of oxygen sensors having different heater arrangements, taken at their oxygen detecting portions.
Figure 16:
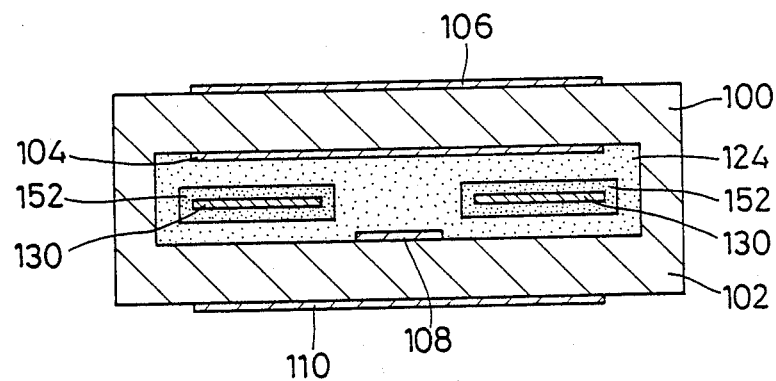

Further modified arrangements of the heater element 130 are shown in FIGS. 15 and 16, wherein the heater element 130 is electrically insulated from the reference electrode 104 and the inner pumping electrode 108. More specifically, at least a portion of the porous layer 124 is made of an electrically insulating material, and the heater element 130 is embedded in the electrically insulating portion of the porous layer 124. For better electrical insulation, it is preferred that the heater element 130 is spaced apart from the inner pumping electrode in the direction parallel to the plane of the porous layer 124. It is further preferred that the heater element 130 is disposed in sufficient distance away from the reference electrode 104 in the direction perpendicular to the plane of the porous layer 124. In the arrangement of FIG. 16, the heater element 130 is surrounded by highly-dense gas-tight layers 152 embedded in the porous layer 124. The highly dense layers 152 facilitate heat dissipation from the heater element 130, thereby enhancing the life expectancy of the heater element. The highly dense layers 152 are made of zirconia or other ceramic materials which have a high electrical resistance, and which have a better sinterability than the porous layer 124.

In the arrangements of FIGS. 15 and 16 wherein the heater element 130 is embedded in the porous layer 124, the heater element 130 may be located substantially in the central part of the sensing element, and the heat transfer from the heater element 130 and the temperature distribution of the sensing element may be improved, as compared with an arrangement wherein the heat transfer from the heater element is effected through a space formed in the sensing element. That is, the presence of the porous layer 124 surrounding the heater element 130 permits improved efficiency of thermal conduction from the heater element 130, and more uniform temperature distribution throughout the sensing element, thus minimizing thermal strain of the sensing element and overheating of the heater element, and consequently resulting in significant improvement in the life expectancy of the heater.

As shown in FIGS. 3-8, and FIGS. 11-14, the measuring and pumping electrodes 64, 106, 110 which are exposed to the external measurement gas are protected by the porous protective layers 82, 112, 114 that are made of alumina or similar ceramic materials with a suitable thickness. These porous ceramic protective layers may be formed by suitable known methods such as plasma spraying or screen printing, or may be preferably formed in such manners as illustrated in FIGS. 17-19.

Figure 17:
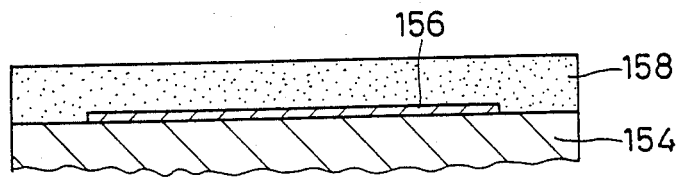
FIGS. 17 through 19 are fragmentary cross sectional views, illustrating different protective layers covering an electrode which is exposed to a measurement gas.

Referring to FIG. 17, reference numeral 154 designates a solid electrolyte body having an electrode 156 which is exposed to the external measurement gas. The electrode 156 is covered by a porous ceramic protective layer 158 having a suitable thickness. This protective layer 158 may be obtained by first forming an unfired ceramic sheet of about 100-500 microns over the unfired electrode 156, in a tape-forming or other method, and then co-firing these ceramic sheet and electrode together with a green sheet of the solid electrolyte body 154. Preferably, the porous ceramic protective layer 158 is made of a ceramic material such as zirconia having the same or nearly equal coefficient of thermal expansion as the solid electrolyte body 154.

The protective layer 158 may be made porous by (1) adding to the ceramic material a large amount of organic substance or binder which disappears during firing, or (2) selecting the ceramic material which has a poorer sinterability than the material of the solid electrolyte body 154. The latter method (2) may be practiced in one of the following three manners: (a) using a ceramic powder having a relatively large grain size; (b) using a zirconia ceramic material (fully stabilized zirconia, or a mixture of fully and partially stabilized zirconia materials) for the porous layer 158, while using partially stabilized zirconia for the solid electrolyte body 154; and (c) using a mixture of a solid electrolyte material, and another ceramic material which has a lower sinterability than the material of the solid electrolyte body 154. In the case of (b) where the porous layer 158 is made of a mixture of the fully and partially stabilized zirconia materials, the porosity of the layer 158 may be selected by changing the mixing ratio. Further, the above method (2) may be practiced by using the above manners (a), (b) and (c) in combination.

Figure 18:
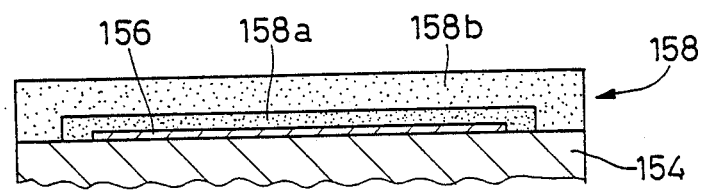
Figure 19:
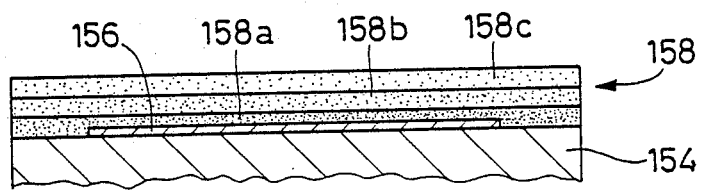

The porous ceramic protective layer 158 shown in FIG. 18 consists of two layers, i.e., an inner layer 158a covering the electrode 156, and an outer layer 158b covering the inner layer 158a. In this case, the inner and outer layers 158a, 158b may have different porosities. Further, the outer layer 158b may be adapted to remove particulate materials contained in the measurement gas, while the inner layer 158a may be adapted to catch toxic materials in a gaseous phase. The porous layer 158 consisting of such two layers may be formed in the same manner as described above. The inner layer 158a may be formed by printing.

The porous ceramic protective layer 158 shown in FIG. 19 consists of three layers, i.e., an inner layer 158a, an intermediate layer 158b and an outer layer 158c. If necessary, the protective layer 158 may consist of four or more layers. These multiple layers of the protective layer 158 may be obtained by forming respective unfired ceramic sheets successively on the electrode 156, or by first preparing a single unfired ceramic sheet consisting of three or more layers which are formed by a tape-forming process, and then placing the unfired ceramic sheet over the unfired electrode 156. In the latter case, the respective layers are formed by a doctor-blade method, using different slurries which have different ceramic grain sizes and different amounts of binders, so that the sinterability or ease of drying of the multiple layers is changed from one layer to another in the direction of their thickness, and so that the dried layers have a continuously varying grain size distribution in the direction of their thickness.

The unfired ceramic sheets or layers for the porous protective layer 158 are fired together with the green sheets of the solid electrolyte body 154. Thus, the porous protective layer 158 firmly bonded to the solid electrolyte body 154 can be obtained. Unlike a porous protective layer conventionally formed by a plasma coating method, the protective layer 158 provides the following advantages: (a) higher yield of the materials (lower cost of fabrication); (b) greater adherence to the solid electrolyte body; (c) larger total thickness, which provides increased effect of protecting the electrode 156 (a relatively thick protective layer formed by plasma coating tend to flake off, while a protective layer to be formed by printing is limited in the maximum thickness); (d) easier formation of multiple layers which have different protective functions, e.g., a rough layer functioning as a filter for removing particulation materials, while a fine layer functioning to trap gaseous phase substances; (e) higher freedom in the selection of materials, permitting the formation of a catalytic layer such as a nickel oxide layer, or a layer containing other desired metals; and (f) easier control of the operating response of the sensing element, by adjusting the porosity and/or thickness of the porous protective layer, so that the amount of the measurement gas to be supplied to the electrode 156, for example, an outer pumping electrode, is sufficient to perform an intended pumping action without affecting the response of the sensor.

The porosity of the porous protective layer 158 is generally between 5 and 90%, preferably between 10 and 50%.

Figure 20:
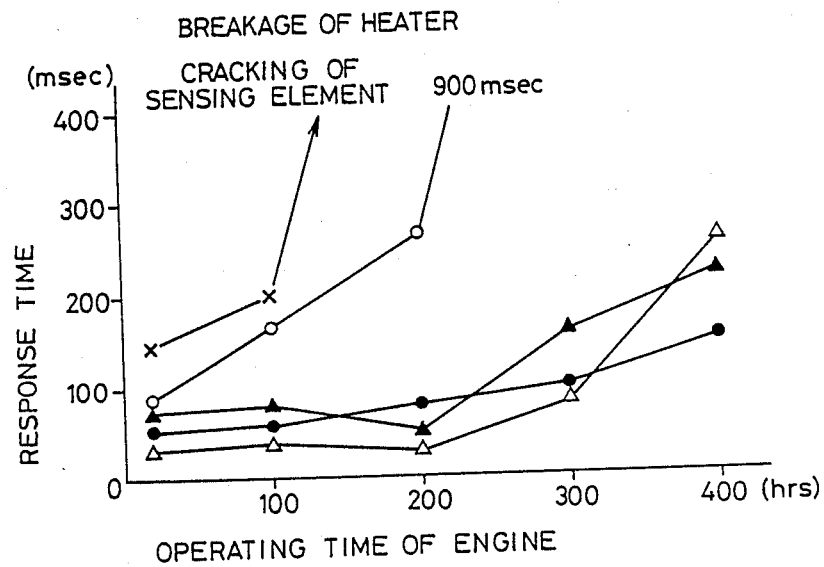
FIG. 20 is a graph showing test results of various oxygen sensors exposed to exhaust gases emitted by engines.

Various oxygen sensors having different constructions and different porous protective layers are indicated in the following table were tested, being exposed to exhaust gases emitted by an engine. The test results are shown in FIG. 20. Oxygen sensor E employs a conventional type sensing element which has a reference gas cavity or passage communicating with the ambient air, and does not have an oxygen pumping cell. Further, the oxygen sensor E has a heater which is positioned at an outer portion of the sensing element, remote from the measuring electrode.

| Sensors | Sensing Element | Porous Protective Layer |
| --- | --- | --- |
| A | As shown in FIG. 12 (Reference oxygen is released through relief holes.) | Formed of spinel, by plasma coating: 100-micron thick |
| B | | Porous ceramic layer as shown in FIG. 17 |
| C | | Porous ceramic layer as shown in FIG. 18 |
| D | As shown in FIG. 14 (Reference oxygen is relief holes.) | Porous ceramic layer as shown in FIG. 17 |
| E | Conventional type (The sensor housing has air-inlet openings, and the element has a reference gas passage.) | Formed of spinel, by plasma coating: 100-micron thick |

The engine used is a 2-liter four-cylinder engine having an oil consumption of 80 cc/Hr. The engine was operated with an air-fuel mixture containing 0.4 g of lead per liter, alternately at 1000 rpm and 4000 rpm for 5 and 15 minutes, respectively. In the 5-min. operation at 1000 rpm, the exhaust gas temperature was within a range of 300°–500° C. In the 15-min. operation at 4000 rpm, the exhaust gas temperature was within a range of 700°–900° C. The durability of the individual oxygen sensors was evaluated from the response time of their sensing element. The results shown in FIG. 20 are average values of measurements obtained on five specimens of each sensor.

The response time of the oxygen sensing elements of the sensors increases as the protective layers of the sensing elements is contaminated or clogged. The graph of FIG. 20 reveals that the sensors having the co-firing porous ceramic layers according to the invention have shorter response times over a comparatively long operating time of the engine, namely, better durability, than the conventional sensor E whose housing has air-inlet openings. The sensor E suffered from cracking of the sensing element (two of five specimens) and brekage of the heater element (one of the five specimens), during the first 100-hour exposure to the exhaust gases.

The five sensors A through E were also subjected to a salt water test, in which the sensors attached to the exhaust pipe of the engine continuously operating at 1000 rpm were exposed to a sprayed mist of salt water every 10 minutes. The number of abnormal outputs of the sensors was counted. The test showed no abnormal outputs on the sensors A–D according to the present invention. However, the conventional sensor E exhibited an abnormal output upon exposure to the first spray of salt water, which caused the salt water to enter the sensor housing through the air-inlet openings.

While the present invention has been described in its preferred embodiments with a certain degree of particularity, it is to be understood that the invention is not limited to the details of the illustrated embodiments, but may be embodied with various changes, modifications and improvements which may occur to those skilled in the art, without departing from the spirit and scope of the present invention.

In the oxygen sensor constructed according to the present invention, reference gas is supplied from the external measurement gas to the reference electrode within the sensing element, by an oxygen pumping action of the sensing element, and is stored in a suitable space or porous structure within the element, whereby the reference electrode is exposed to the stored oxygen as the reference gas. Thus, the sensor does not require air-inlet openings formed through its housing, for introducing the ambient air as the reference gas into the interior of the sensing element, and consequently the sensor can be a completely fluid tight structure, except the oxygen detecting portion exposed to the measurement gas. Therefore, the instant oxygen sensor can be made simple in construction, and does not suffer from electrical insulation failure or trouble due to exposure to water, salt water or muds, which may cause erroneous output signals.

Further, the sensing element of the present oxygen sensor does not require a reference-gas space or passage which communicates with the ambient air through the air-inlet openings in the sensor housing. According to the invention, a space for storing the reference gas pumped from the external measurement gas is partially or fully filled with a porous layer made of alumina or similar ceramic materials. This ceramic porous layer contributes to increasing the strength of the sensing element, and avoiding defective sensors which may result from otherwise possible collapse of the oxygen storage space (reference-gas space or passage as provided in the conventional sensors) during the process of fabrication, thereby improving the yield of the manufacture of the sensors. These are industrially significant advantages offered by the present invention.

What is claimed is:

1. An electrochemical device for detecting a measurement fluid, comprising:
    a planar solid electrolyte body;
    a first electrode formed on said planar solid electrolyte body, and substantially exposed to said measurement fluid;
    a second electrode formed on said planar solid electrolyte body, and substantially isolated from said measurement fluid;
    a porous layer disposed in direct contact with said second electrode;
    a heat-generating element embedded within said porous layer; and
    reference-gas supply means for supplying said porous layer with a reference gas, comprising an electrochemical reference-gas supply cell including an inner electrode disposed in direct contact with said porous layer, and an outer electrode, said reference-gas supply means further comprising means for applying an electric current between said inner and outer electrodes to pump said reference gas into said porous layer,
    said planar solid electrolyte body, said first and second electrodes, said heat-generating element and said electrochemical cell being superimposed on each other in parallel relation with each other, such that said heat-generating element and said inner electrode are spaced apart from each other in a direction parallel to a plane of said planar solid electrolyte body, said outer electrode of said electrochemical cell having a larger surface area than said inner electrode, and partially overlapping said heat-generating element as viewed in a plane parallel to said direction.

2. An electrochemical device according to claim 1, wherein said porous layer includes an electrically insulating portion in which said heater is embedded.

3. An electrochemical device according to claim 1, wherein said means for applying an electric current of said reference-gas supply means comprises a constant-voltage power source.

4. An electrochemical device according to claim 1, wherein said means for applying an electric current of said reference-gas supply means comprises a constant-current power source.

5. An electrochemical device according to claim 1, wherein a portion of said porous layer includes a dense gas-tight material in which said heat-generating element is at least partially embedded.

6. An electrochemical device according to claim 1, further comprising, a heater power source for energizing said heat generating element, and a voltage divider for applying a fraction of a total voltage of said heater power source between said inner and outer electrodes, said heater power source and said voltage divider cooperating to constitute said means for applying an electric current.

7. An electrochemical device according to claim 1, further comprising a porous protective layer through which said first electrode is exposed to said measurement fluid.

8. An electrochemical device according to claim 7, wherein said porous protective layer is formed by plasma spraying.

9. An electrochemical device according to claim 7, wherein said porous protective layer consists of a porous ceramic layer which is obtained by co-firing an unfired ceramic layer formed by printing on an unfired layer of said first electrode, together with an unfired sheet of said solid electrolyte body.

10. An electrochemical device according to claim 7, wherein said porous protective layer consists of a porous ceramic layer which is obtained by preparing an unfired ceramic sheet, placing said unfired ceramic sheet on an unfired layer of said first electrode, and then co-firing said unfired ceramic sheet together with an unfired sheet of said planar solid electrolyte body.

11. An electrochemical device according to claim 1, further comprising means for restricting a diffusion of said reference gas from said porous layer into said measurement fluid or an external space outside said electrochemical device which comprises said planar solid electrolyte body, said first and second electrodes, said porous layer, said heat-generating element, and said reference-gas supplying means.

12. An electrochemical device according to claim 11, further comprising a sensor housing in which said electrochemical device is fixed in place with a filler, said means for restricting a diffusion of said reference gas comprising said filler.

13. An electrochemical device for detecting a measurement fluid, comprising:
   at least two planar solid electrolyte bodies;
   diffusion-resistance means having a predetermined diffusion resistance to said measurement fluid;
   a first electrode formed on one of said at least two planar solid electrolyte bodies, and exposed to said measurement fluid through said diffusion-resistance means;
   a second electrode formed on said one of said at least two planar solid electrolyte, bodies and substantially isolated from said measurement fluid;
   a third electrode formed on another one of said at least two planar solid electrolyte bodies, and exposed to said measurement fluid through said diffusion-resistance means;
   a fourth electrode formed on said another one of said at least two planar solid electrolyte bodies, and substantially directly exposed to said measurement fluid;
   a fifth electrode formed on said one of said at least two planar solid electrolyte bodies, and substantially directly exposed to said measurement fluid;
   a porous layer disposed in direct contact with said second electrode;
   a heat-generating element embedded within said porous layer;
   means for applying an electric current so as to flow from said electrode to said fifth electrode;
   voltage detecting means connected between said second electrode and said first electrode, for detecting a voltage therebetween; and
   current regulating means connected between said third and fourth electrodes, for controlling an atmosphere adjacent to said first electrode, said heat-generating element and said second electrode being spaced apart from each other in a direction parallel to a plane of said second electrode, and said fifth electrode having a larger surface area than said second electrode, and partially overlapping said heat-generating element as viewed in a plane parallel to the plane of said second electrode.

14. An electrochemical device according to claim 13, wherein said porous layer includes an electrically insulating portion in which said heater is embedded.

15. An electrochemical device according to claim 13, wherein said first and third electrodes define therebetween a thin flat space communicating with said measurement fluid, said thin flat space constituting said diffusion-resistance means.

16. An electrochemical device according to claim 13, further comprising a porous structure disposed between said first and third electrodes, to function as said diffusion-resistance means.

17. An electrochemical device according to claim 13, wherein said means for applying an electric current comprises a constant-voltage power source.

18. An electrochemical device according to claim 13, wherein said means for applying an electric current comprises a constant-current power source.

19. An electrochemical device according to claim 13, further comprising a heater power source for energizing said heat-generating element, and a voltage divider for applying a fraction of a total voltage of said heater power source between said first and second electrodes, said heater power source and said voltage divider cooperating to constitute said means for applying an electric current.

20. An electrochemical device according to claim 13, further comprising at least one porous protective layer through which at least one of said first, third, fourth and fifth electrodes is exposed to said measurement fluid, respectively.

21. An electrochemical device according to claim 20, wherein each of said at least one porous protective layers is formed by plasma spraying.

22. An electrochemical device according to claim 20, wherein each of said at least one porous protective layers consist of a porous ceramic layer which is obtained by co-firing an unfired ceramic layer formed by printing on an unfired layer electrode, together with an unfired sheet of said planar solid electrolyte body.

23. An electrochemical device according to claim 20, wherein each of said at least one porous protective layers consists of a porous ceramic layer which is obtained by preparing an unfired ceramic sheet, placing said unfired ceramic sheet on an unfired layer of the corresponding one of said first, third, fourth and fifth electrodes, and then co-firing said unfired ceramic sheet together with an unfired sheet of said planar solid electrolyte body.

24. An electrochemical device according to claim 13, further comprising means for restricting a diffusion of a reference gas from said porous layer into said measurement fluid or an external space outside said electrochemical device which comprises said planar solid electrolyte body, said first and second electrodes and said porous layer.

25. An electrochemical device according to claim 24, further comprising a sensor housing in which said sensing element is fixed in place with a filler, said means for restricting a diffusion of a reference gas comprising said filler.

26. An electrochemical device for detecting a measurement fluid, comprising:
   a planar solid electrolyte body;
   a first electrode formed on said planar solid electrolyte body, and substantially exposed to said measurement fluid;
   a second electrode formed on said planar solid electrolyte body, and substantially isolated from said measurement fluid;
   a porous layer disposed adjacent to said second electrode;
   a heat-generating element embedded within said porous layer; and
   reference-gas supply means for supplying said porous layer with a reference gas, comprising an electrochemical reference-gas supply cell including an inner electrode disposed in direct contact with said porous layer, and an outer electrode, said reference-gas supply means further comprising means for applying an electric current between said inner and outer electrodes to pump said reference gas into said porous layer,
   said planar solid electrolyte body, said first and second electrodes, said heat-generating element and said electrochemical cell being superimposed on each other in parallel relation with each other, such that said heat-generating element and said inner electrode are spaced apart from each other in a direction parallel to a plane of said planar solid electrolyte body, said outer electrode of said electrochemical cell having a larger surface area than said inner electrode, and partially overlapping said heat-generating element as viewed in a plane parallel to said direction.

* * * * *